US010416125B2

(12) United States Patent
Lee et al.

(10) Patent No.: US 10,416,125 B2
(45) Date of Patent: Sep. 17, 2019

(54) METHOD FOR DETERMINING CONCENTRATION AND PRESSURE OF RESPECTIVE GAS OF MULTI-GAS

(71) Applicant: SOGANG UNIVERSITY RESEARCH FOUNDATION, Seoul (KR)

(72) Inventors: Tae Soo Lee, Gyeonggi-do (KR); Seung Hyun Ryu, Seoul (KR); Hyun Jin Cho, Jeju-si (KR); Seung Kwon Oh, Namyangju-si (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 287 days.

(21) Appl. No.: 15/630,338

(22) Filed: Jun. 22, 2017

(65) Prior Publication Data
US 2018/0196015 A1    Jul. 12, 2018

(30) Foreign Application Priority Data
Jan. 12, 2017 (KR) .......................... 10-2017-0005522

(51) Int. Cl.
*G01N 29/44*    (2006.01)
*G01N 29/024*   (2006.01)
(Continued)

(52) U.S. Cl.
CPC .......... *G01N 29/4463* (2013.01); *G01L 11/06* (2013.01); *G01N 29/024* (2013.01);
(Continued)

(58) Field of Classification Search
CPC . G01N 2291/0215; G01N 2291/02809; G01N 29/024; G01N 29/326;
(Continued)

(56) References Cited

U.S. PATENT DOCUMENTS

| 8,495,913 B2* | 7/2013 | Partington | .......... G01F 23/2962 |
| | | | 73/290 V |
| 2011/0155131 A1* | 6/2011 | Bottom | ............... A61M 16/104 |
| | | | 128/203.14 |

(Continued)

FOREIGN PATENT DOCUMENTS

| JP | 2001-255313 A | 9/2001 |
| JP | 2015-158403 A | 9/2015 |
| KR | 10-2010-0023911 A | 3/2010 |

*Primary Examiner* — Francis C Gray
(74) *Attorney, Agent, or Firm* — Rabin & Berdo, P.C.

(57) ABSTRACT

A method for determining concentration and pressure of respective gas consisting of multi-gas using emitting and receiving of ultrasound includes: measuring a reference ultrasound flight time; measuring ultrasound flight times at plural concentrations, temperatures and pressures; obtaining an ultrasound flight time table comprising ultrasound flight time change values which are differences between the reference ultrasound flight time, which varies according to parameters of concentration, temperature and pressure, and the measured ultrasound flight time; obtaining an ultrasound amplitude table comprising ultrasound amplitude values of a waveform of a predetermined sequence of the received ultrasound waveform at plural concentrations, temperatures and pressures in a state that concentration, temperature and pressure of the target respective gas are parameters; and calculating the concentration and the pressure of the target gas based on performing temperature compensations for the ultrasound flight time change values and the ultrasound amplitude values.

2 Claims, 10 Drawing Sheets

(51) Int. Cl.
*G01L 11/06* (2006.01)
*G01N 33/00* (2006.01)
*G01N 29/32* (2006.01)

(52) U.S. Cl.
CPC ....... *G01N 29/326* (2013.01); *G01N 29/4436* (2013.01); *G01N 33/0062* (2013.01); *G01N 2291/0215* (2013.01); *G01N 2291/02809* (2013.01)

(58) Field of Classification Search
CPC ........... G01N 29/4436; G01N 29/4463; G01N 33/0062; G01L 11/06
See application file for complete search history.

(56) References Cited

U.S. PATENT DOCUMENTS

| | | | |
|---|---|---|---|
| 2015/0209546 A1* | 7/2015 | Pernikoff | A61M 16/01 128/202.27 |
| 2017/0176582 A1* | 6/2017 | Bjorkengren | G01S 11/16 |
| 2017/0205385 A1* | 7/2017 | Prystupa | G01N 33/12 |

* cited by examiner

METHOD FOR DETERMINING CONCENTRATION AND PRESSURE OF RESPECTIVE GAS OF MULTI-GAS

CROSS-REFERENCE TO RELATED APPLICATION

This application claims priority to and the benefit of Korean Patent Application No. 10-2017-0005522 filed in the Korean Intellectual Property Office on Jan. 12, 2017, the entire contents of which are incorporated herein by reference.

TECHNICAL FIELD

The present invention relates to a method for determining concentration and pressure of respective gas consisting multi-gas.

BACKGROUND ART

A method of calculating concentration of multi-gas which is composed of multiple gases components of which are already known using ultrasound has been disclosed. By generating ultrasound in a space which is filled with multi-gas and detecting reflected ultrasound and calculating time of flight (TOF) between sending and receiving ultrasound, concentration of respective gas of multi-gas can be determined.

However, in a conventional method concentration of respective gas of multi-gas is calculated through complicated calculation and there is a limitation that pressure of respective gas cannot be determined together. Further, although concentration of respective gas is influenced by pressure thereof, the conventional method calculates concentration without consideration of pressure, so it is difficult to calculate precise concentration.

DETAILED DESCRIPTION OF THE INVENTION

Technical Problem

The present invention has been made in an effort to provide a method for determining concentration and pressure of respective gas consisting of multi-gas which can reflect the effect of the pressure on the concentration.

Technical Solution

According to an exemplary embodiment of the present invention, a method for determining concentration and pressure of respective gas consisting of multi-gas using emitting and receiving of ultrasound includes: measuring a reference ultrasound flight time at a reference concentration, a reference temperature and a reference pressure for a target respective gas among respective gases consisting the multi-gas which is filled in a measuring space using an emitted ultrasound waveform and a received ultrasound waveform; measuring ultrasound flight times at plural concentrations, temperatures and pressures in a state that concentration, temperature and pressure of the target respective gas are parameters; obtaining an ultrasound flight time table comprising ultrasound flight time change values which are differences between the reference ultrasound flight time, which varies according to parameters of concentration, temperature and pressure, and the measured ultrasound flight time; obtaining an ultrasound amplitude table comprising ultrasound amplitude values of a waveform of a predetermined sequence of the received ultrasound waveform at plural concentrations, temperatures and pressures in a state that concentration, temperature and pressure of the target respective gas are parameters; and calculating the concentration and the pressure of the target gas based on performing temperature compensations for the ultrasound flight time change values and the ultrasound amplitude values.

The calculating of the concentration and the pressure of the target gas may include: obtaining a temperature compensation equation for an ultrasound flight time which makes the ultrasound flight time change values at the plural temperatures become the ultrasound flight time change value at the reference temperature; obtaining a temperature compensation equation for an ultrasound amplitude which makes the ultrasound amplitude values at the plural temperatures become the ultrasound amplitude value at the reference temperature; converting an ultrasound flight time change value measured at an arbitrary measuring temperature and an ultrasound amplitude value measured at an arbitrary measuring temperature into an ultrasound flight time change value at the reference temperature and an ultrasound amplitude value respectively by putting the same into the temperature compensation equation for the ultrasound flight time change value and the temperature compensation equation for the ultrasound amplitude respectively; and calculating the concentration and the pressure of the target gas by nonlinear equations using the ultrasound flight time change values at the reference temperature and the ultrasound amplitude values at the reference temperature.

Advantageous Effects

According to the present invention, since an effect of the pressure to the concentration is considered, the concentration and the pressure of a gas consisting of multi-gas can be precisely determined.

DETAILED DESCRIPTION OF THE EMBODIMENTS

An embodiment of the present invention will be described with reference to the accompanying drawings hereinafter.

A method for determining concentration and pressure of respective gas of multi-gas according to an embodiment of the present invention determines the concentration and the pressure of the respective gas consisting of multi-gases using transmitting and receiving of ultrasound.

Figure 1:
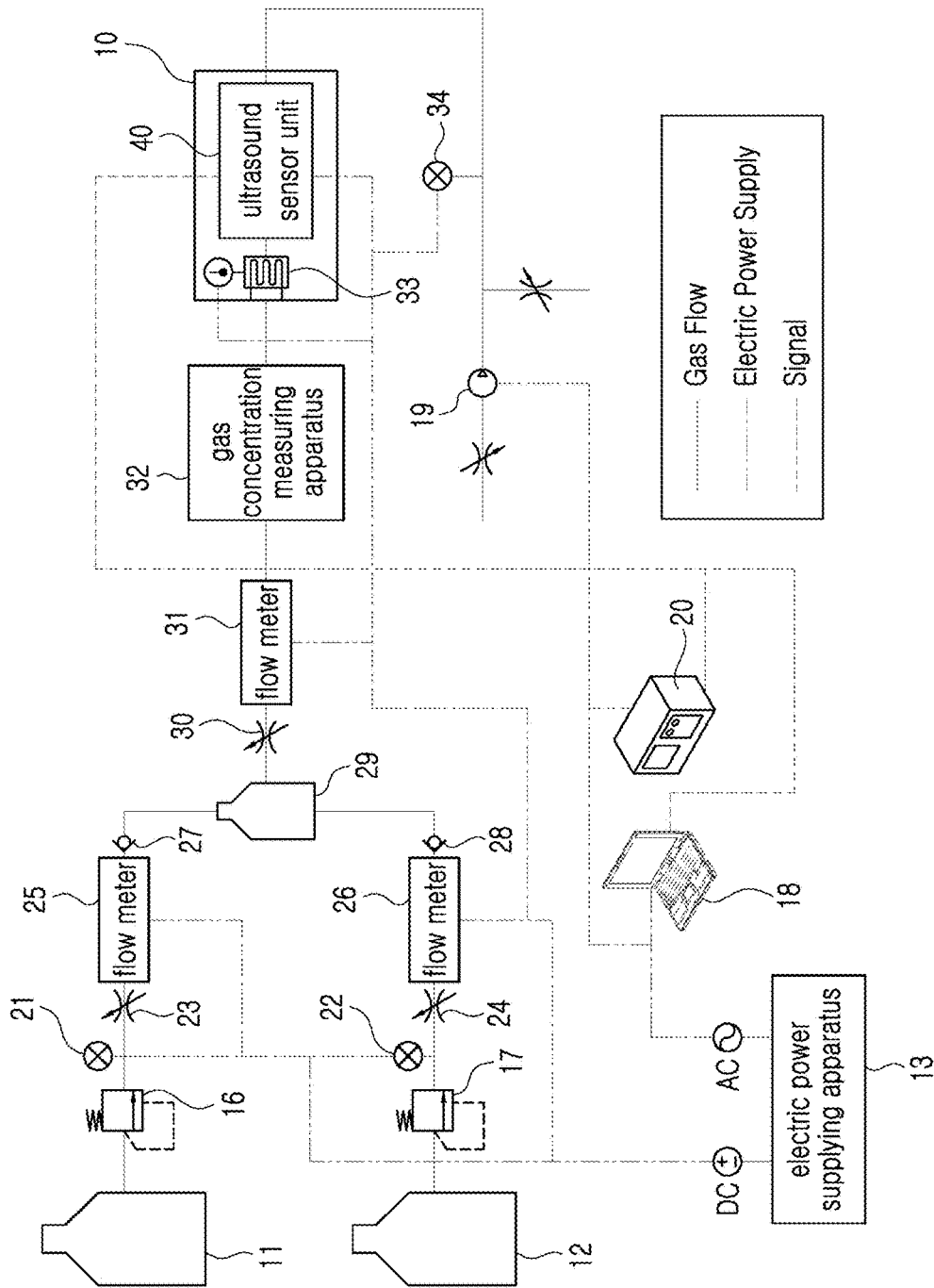
FIG. 1 shows an example of an experimental device which can perform a method for determining concentration and pressure of respective gas of multi-gas according an embodiment of the present invention.
Figure 2:
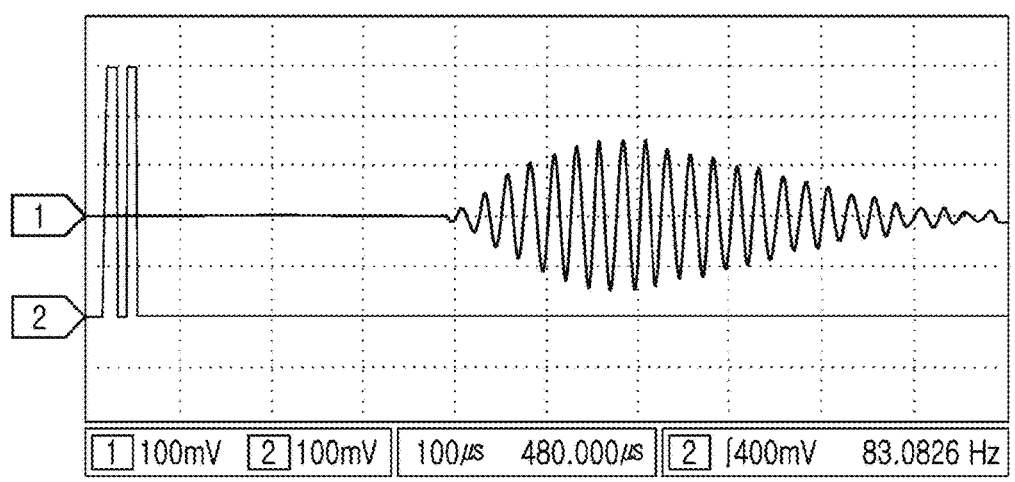
FIG. 2 shows a wave form of received ultrasound output from an oscilloscope of an experimental device.

Referring to FIG. 1, a method for determining concentration and pressure of respective gas of multi-gas may be performed using an experimental equipment including a device for supplying a plurality of gases into a gas chamber in which multi-gas is filled. For example, the multi-gas may be a binary gas including oxygen and nitrogen, and an example in which a multi-gas is a binary gas including oxygen and nitrogen will be described.

For example, referring to FIG. 1, the experimental equipment may include an oxygen tank 11 and a nitrogen tank 12 which contain oxygen and nitrogen respectively. Gas pressure regulators 16 and 17 which respectively regulate the pressures of the supplied oxygen and the supplied nitrogen may be provided respectively to output passages of the oxygen tank 16 and the nitrogen tank 17. Further, pressure gauges 21 and 22 which respectively detect the pressures of oxygen and nitrogen having passed the gas pressure regulators 16 and 17. Further, flow regulating valves 23 and 24 which respectively regulate flow amount of oxygen and nitrogen may be provided, and flow meters 25 and 26 which respectively detect flow amount of oxygen and nitrogen having passed the flow regulating valves 23 and 24. Oxygen and nitrogen having passed the flow meters 25 and 26 respectively pass through check valves 27 and 28 and are then supplied to a mixed gas tank 29. A mixed gas discharged from the mixed gas tank 29 is supplied to a gas chamber 10 via a flow regulating valve 30 and a flow meter 31.

At this time, a gas concentration detector 32 for detecting the concentration of a specific gas (e.g., oxygen) consisting of the multi-gas which is supplied to the gas chamber 10 may be provided. In addition, a heat exchanger 33 which is configured to undergo heat exchange with a gas supplied to the gas chamber 10 to regulate the temperature of the gas to a desired temperature.

An ultrasound sensor unit 40 may be disposed in the gas chamber 10. The ultrasound sensor unit 40 may include an ultrasound emitter which generates and emits ultrasound and an ultrasound receiver which receives ultrasound being returned after being reflected. In addition, the ultrasound sensor unit 40 may include a temperature sensor for detecting a temperature of gas in the gas chamber 10. Also, a pressure gauge 34 for detecting a pressure of gas in the gas chamber 10 may be provided. Further, a pump 19 which discharges gas in the gas chamber 10 to form negative pressure.

Further, an electric power supplying device 13, a computer 18 for calculation, an oscilloscope 20 may be provided.

The ultrasound emitter of the ultrasound sensor unit 40 may include an ultrasound transducer which receives a pulse electric power from the outside to undergo ultrasound vibration to generate ultrasound, and the ultrasound receiver may be a sensor which receives ultrasound which was emitted from the ultrasound emitter and has returned after being reflected by an inner wall of the gas chamber or a reflecting plate inside the gas chamber and outputs a corresponding electrical signal. At this time, the output electrical signal of the ultrasound receiver may be input into the oscilloscope 20, and the oscilloscope 20 may output a waveform which corresponds to the electrical signal corresponding to the physical signal of the ultrasound received by the ultrasound receiver. An example of the ultrasound waveform input into the oscilloscope 20 is shown.

Figure 10:
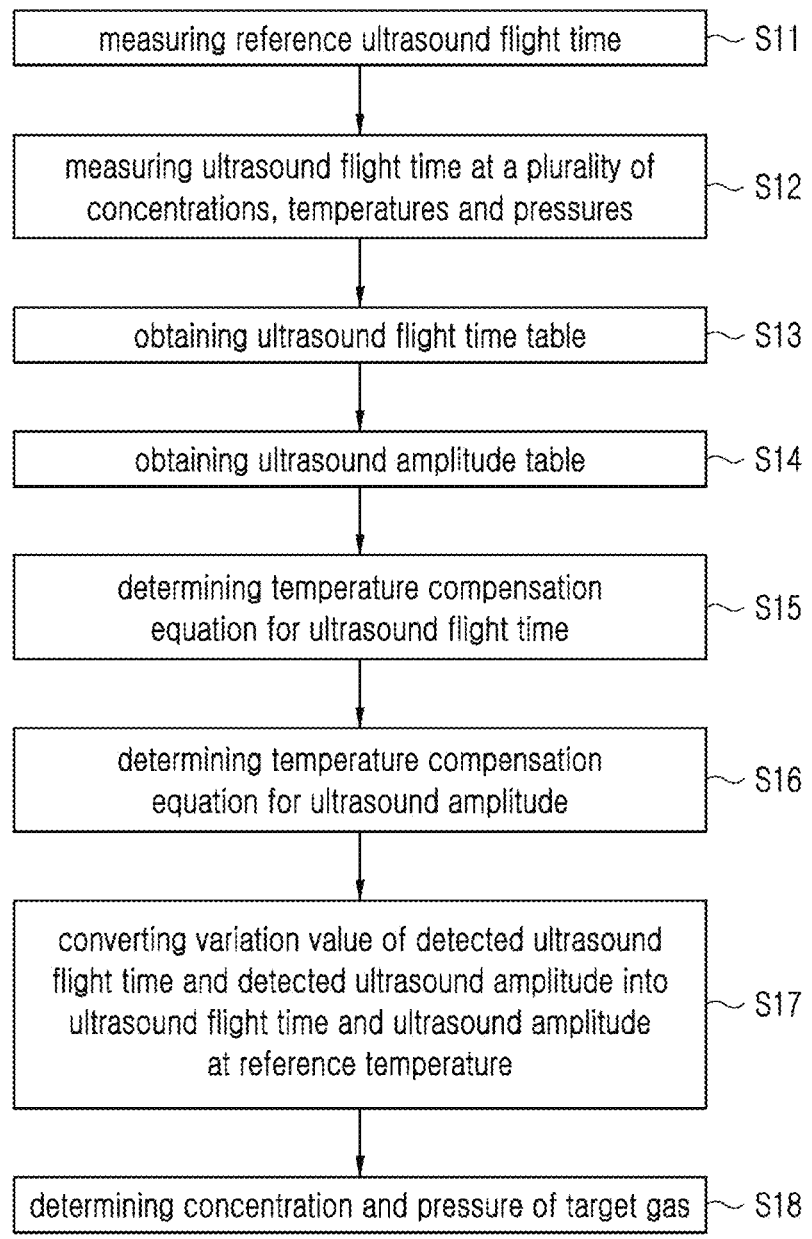
FIG. 10 is a schematic flow chart of a method for determining concentration and pressure of respective gas of multi-gas according to an embodiment of the present invention.

First, a method for determining concentration and pressure of respective gas of multi-gas according to an embodiment of the present invention will be approximately described referring to FIG. 10.

A reference ultrasound flight time is measured at a reference concentration, a reference temperature and a reference pressure for a target respective gas among gases consisting of multi-gas filled in the measuring space at step S11. An ultrasound flight time is measured at plural concentrations, temperatures and pressures in a state that concentration, temperature and pressure of the target respective gas are parameters. Then, at step S13, an ultrasound flight time table which is composed of ultrasound flight time change values which are differences between the reference ultrasound flight time measured at step S11 and the ultrasound flight time measured at step S12 is obtained. Further, at step S14, an ultrasound amplitude table which is composed of amplitudes of waveforms of predetermined sequence of ultrasound waveforms which are received at plural concentrations, temperatures and pressures in a state that concentration, temperature and pressure of the target respective gas are parameters is obtained.

Subsequently, temperature compensations are performed respectively on the ultrasound flight time change value and the ultrasound magnitude value, and the concentration and the pressure of the target gas are determined based on these. Concretely, at step S15, an ultrasound flight time temperature compensation equation which converts the ultrasound flight time change values at plural temperatures into the ultrasound flight time change value at the reference temperature is obtained. Also, at step S16, an ultrasound amplitude temperature compensation equation which converts the ultrasound amplitude values at plural temperatures into the ultrasound amplitude value at the reference temperature is obtained. Subsequently, an ultrasound flight time change value which is measured at arbitrary measuring temperature and an ultrasound amplitude value which is measured at arbitrary measuring temperature are applied respectively into the ultrasound flight time temperature compensation equation and the ultrasound amplitude temperature equation so as to be converted into the ultrasound flight time change value and the ultrasound amplitude value at the reference temperature, at step S17. Subsequently, using the ultrasound flight time change values at the reference temperature and the ultrasound amplitude values at the reference temperature, the concentration and the pressure of the target gas are calculated by nonlinear equations at step S18.

Hereinafter, a method for determining concentration and pressure of respective gas of multi-gas according to an embodiment of the present invention will be described in detail.

First, a reference ultrasound flight time at a reference concentration, a reference temperature and a reference pressure is measured for the target respective gas among gases consisting of the multi-gas. That is, the reference ultrasound flight time is a time that is required for an ultrasound emitted from the ultrasound emitter to return to the ultrasound receiver under reference conditions. For example, using the emitted ultrasound waveform and the received ultrasound waveform of the oscilloscope, the reference ultrasound flight time which is a time difference between the emitting time point and the receiving time point of the ultrasound can be measured. At this time, the reference concentration may be 20%, the reference temperature may be a 293K and the reference pressure may be 1 atmosphere.

Subsequently, ultrasound flight times are measured at plural concentrations, temperatures and pressures in a state that concentration, temperature and pressure of the target respective gas are parameters. At this time, the measured ultrasound flight times are obtained by being measured in plural times under plural concentrations, plural temperatures and plural pressures. For example, in case the measurements are performed for five concentrations, five temperatures and five pressures, 75 measurements are performed and thus 75 measured ultrasound flight times are obtained.

Subsequently, an ultrasound flight time table consisting of an ultrasound flight time change value $\Delta T_{of}$ which is the difference between the reference ultrasound flight time and the measured ultrasound flight time is obtained. That is, the ultrasound flight time table is obtained, and the ultrasound flight time table includes values of difference between the reference ultrasound flight time and the ultrasound flight time measured at plural concentrations, temperatures and pressures.

Figure 3:
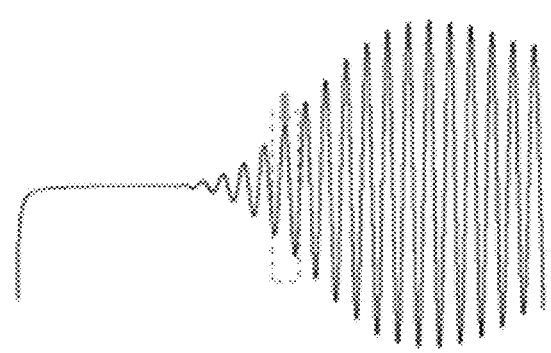
FIG. 3 is a drawing for explaining processes for obtaining ultrasound amplitude table with an amplitude of a waveform of a predetermined sequence in a received ultrasound waveform.

The ultrasound amplitude table is obtained in a way similar to a method of obtaining the ultrasound flight time table. That is, the ultrasound amplitude table consisting of ultrasound amplitude $A_{mp}$ of a wave of a predetermined sequence of a waveform of the received ultrasound at plural concentrations, temperatures and pressures in a state that concentration, temperature and pressure of the target respective gas are parameters is obtained. At this time, as shown in FIG. 3, the ultrasound amplitude table can be made with the amplitude of n-th ultrasound wave of the received ultrasound. That is, the ultrasound amplitude table may include the amplitude data of the n-th wave of the ultrasound received under plural concentrations, temperatures and pressures.

In an embodiment of the present invention, in order to determine the concentration and the pressure of the target gas from the two parameters, the ultrasound flight time change vale $\Delta T_{of}$ and the ultrasound amplitude $A_{mp}$, a curved surface function of the ultrasound flight time change vale $\Delta T_{of}$ and the ultrasound amplitude $A_{mp}$ at the reference temperature are used. That is, the ultrasound flight time change vale $\Delta T_{of}$ and the ultrasound amplitude $A_{mp}$ can be expressed as a function of temperature, concentration and pressure, and theses values are influenced by temperature, so by eliminating temperature parameter by the temperature compensation, the concentration and the pressure can be determined. After the temperature compensation, the ultrasound flight time change vale $\Delta T_{of}$ and the ultrasound amplitude $A_{mp}$ become a function of concentration and pressure.

Figure 4A:
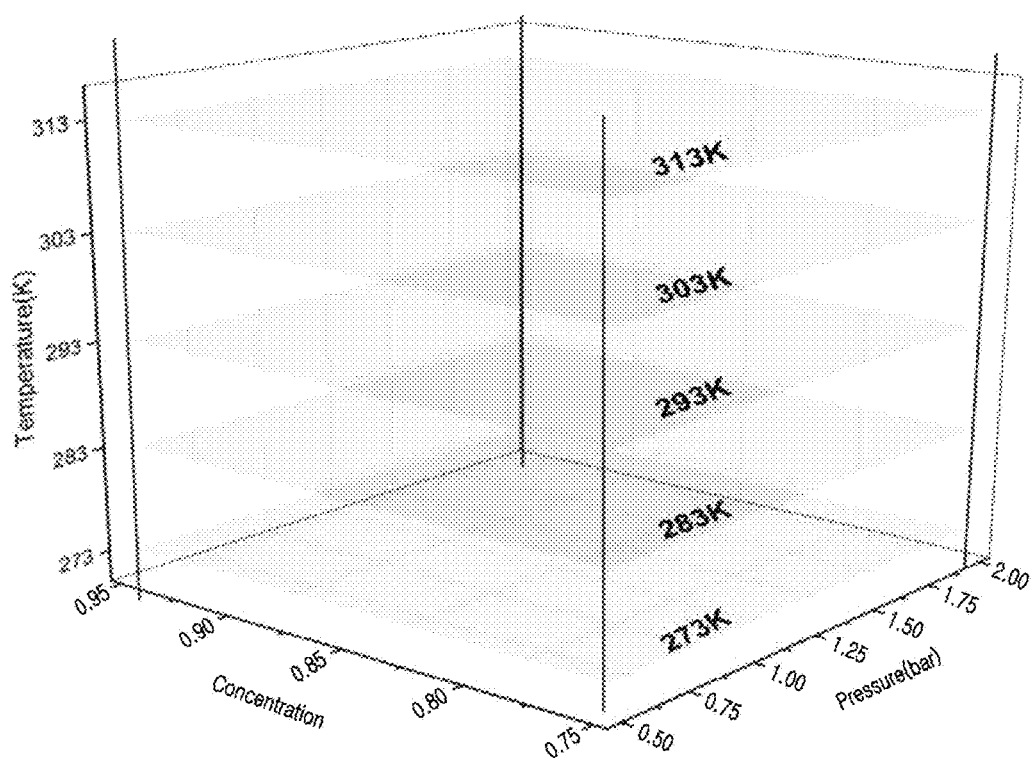
FIGS. 4A and 4B are drawings for explaining processes for temperature calibration with respect to an ultrasound flight time value and an ultrasound amplitude value.
Figure 4B:
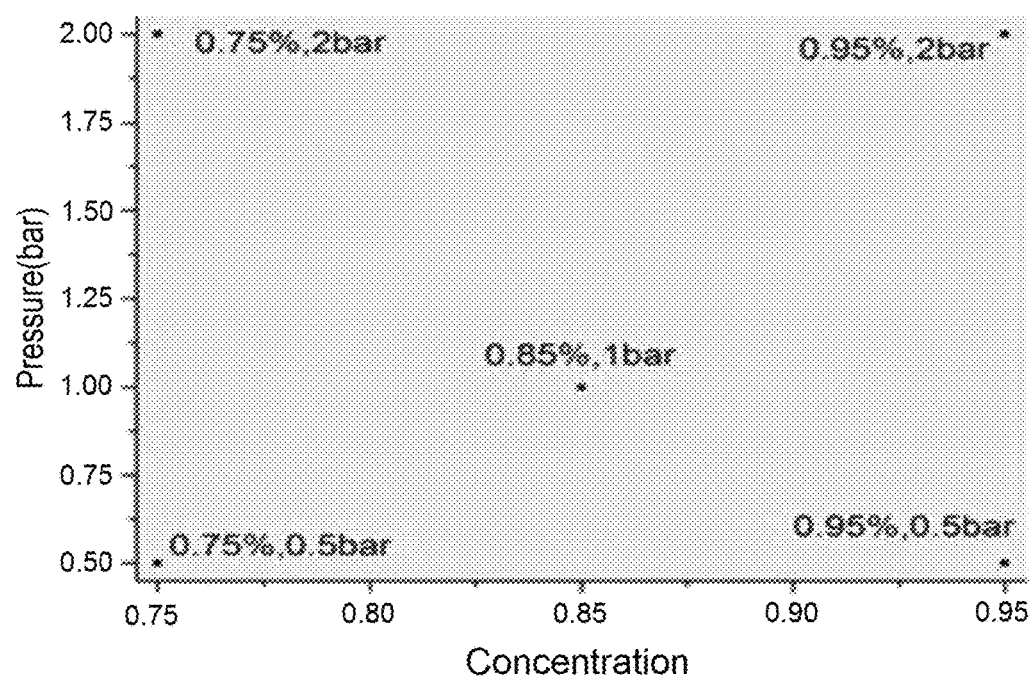

The temperature compensation of the ultrasound flight time change value will be explained referring to FIGS. 4A, 4B and FIG. 5. FIGS. 4A and 4B shows the data structure of the ultrasound flight time change value table, and as shown in FIGS. 4A and 4B, the ultrasound flight time change value table includes the ultrasound flight time change values measured at concentrations, pressures and temperatures. In case of five measuring temperatures, the respective ultrasound flight time change values at the combinations of concentrations, pressures and temperatures corresponding to the five surfaces shown in FIG. 4A are included. In order to remove the influence of the temperature, a surface function which makes the ultrasound flight time change value as a function of the concentration and the pressure at the reference temperature (e.g., 293K) is obtained. At this time, as shown in FIG. 4B, instead of all concentrations and pressures, the temperature compensation may be performed by selecting five representative values. Such a temperature compensation may be performed using a numerical analysis program such as MATLAB.

Figure 5:
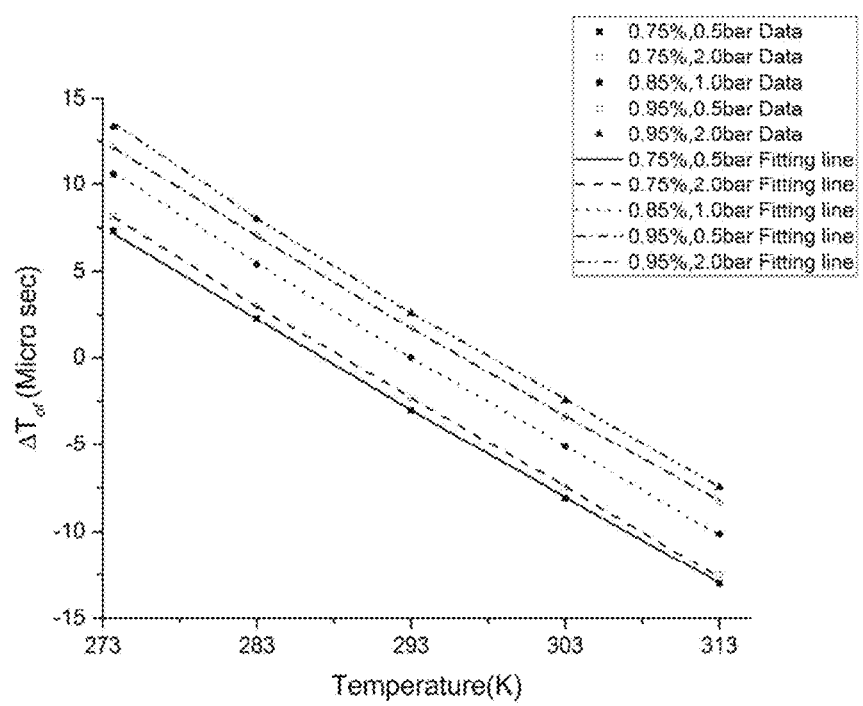
FIG. 5 is a drawing for explaining processes of determining a temperature calibration equation of an ultrasound flight time change value.

Referring to FIG. 5, an ultrasound flight time change value under a specific pressure and a specific concentration varies in response to a temperature, and a temperature compensation equation for an ultrasound flight time change value which makes an ultrasound flight time change value at all temperatures becomes the ultrasound flight time change value at the reference temperature (e.g., 293K) is obtained.

Figure 6:
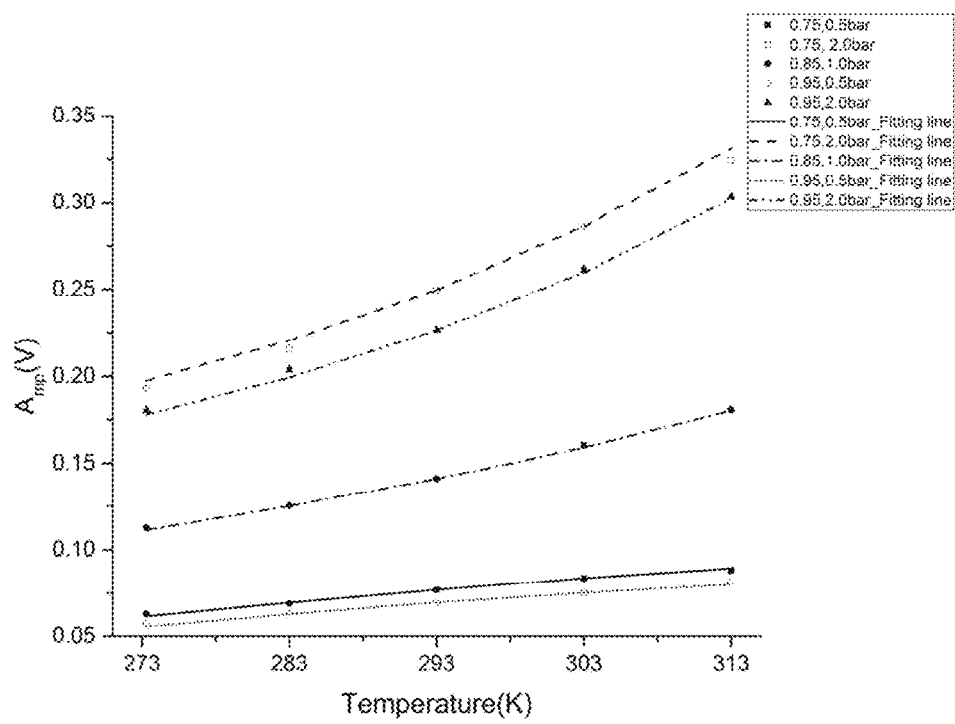
FIG. 6 is a drawing for explaining processes of determining a temperature calibration equation of an ultrasound amplitude value.

Similarly, referring to FIG. 6, an ultrasound amplitude value under a specific pressure and a specific concentration varies in response to a temperature, and a temperature compensation equation for an ultrasound amplitude value which makes an ultrasound amplitude value at all temperatures becomes the ultrasound amplitude value at the reference temperature (e.g., 293K) is obtained.

Subsequently, an ultrasound flight time change value and an ultrasound amplitude value are detected in a state that the target gas has been injected, and a temperature at the time is also detected. By putting the detected temperature and the detected ultrasound flight time change value in the temperature compensation equation for the ultrasound flight time change value, an ultrasound flight time change value at the reference temperature of the target gas can be calculated, and by putting the detected temperature and the detected ultrasound amplitude in the temperature compensation equation for the ultrasound amplitude value, an ultrasound amplitude value at the reference temperature of the target gas can be calculated.

Figure 7:
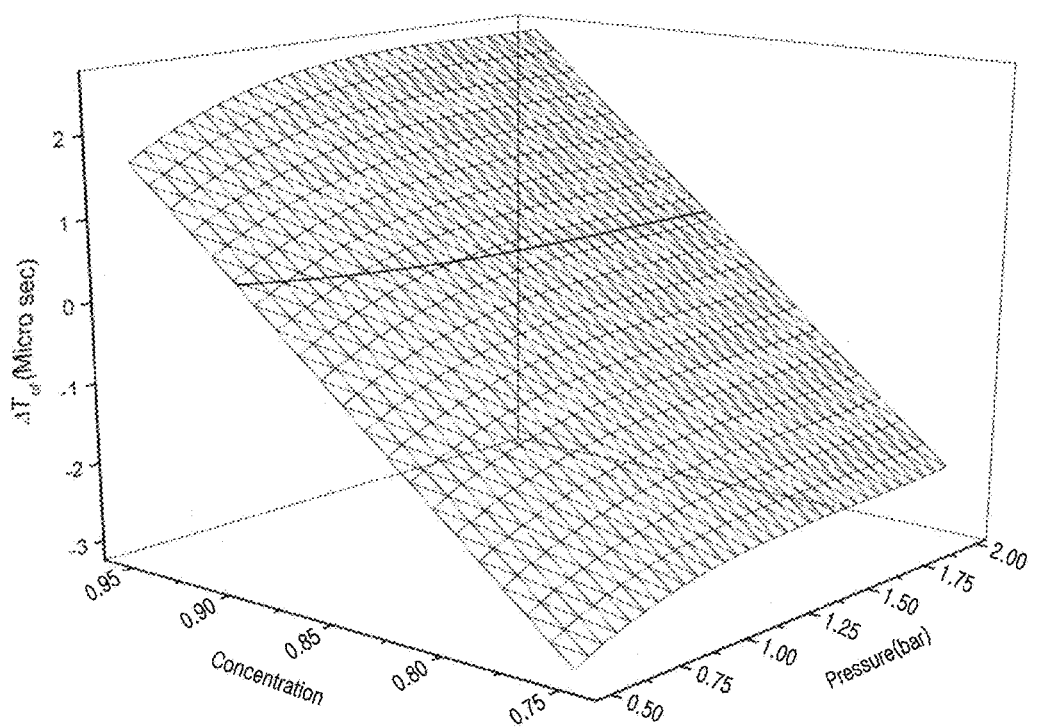
FIG. 7 shows an example of a curved surface of an ultrasound flight time change value contoured at a reference temperature.
Figure 8:
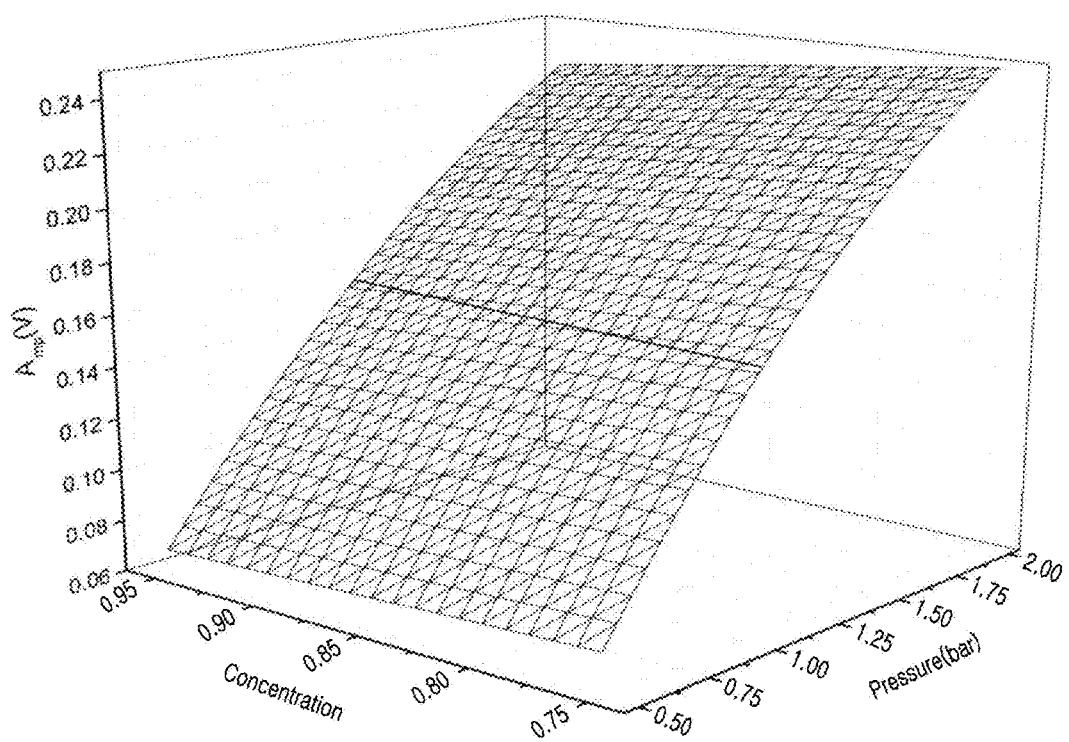
FIG. 8 shows an example of a curved surface of an ultrasound amplitude value contoured at a reference temperature.
Figure 9:
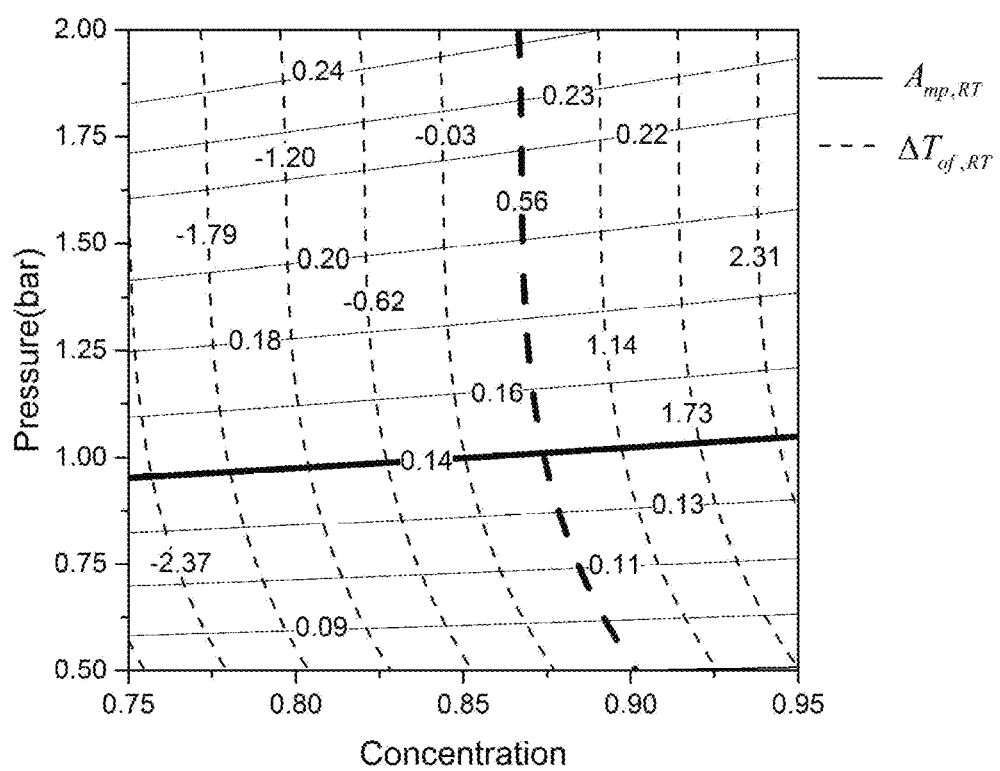
FIG. 9 is a drawing exemplarily showing an ultrasound flight time change value and an ultrasound amplitude value by a temperature calibration equation of an ultrasound flight time change value and a temperature calibration equation of an ultrasound amplitude value according to an embodiment of the present invention.

Subsequently, a curved surface of the ultrasound flight time change values at the reference temperature and a curved surface of the ultrasound amplitude values at the reference temperature are contoured to a surface of the concentration and the pressure, and the concentration and the pressure of the target gas can be calculated using the contoured concentration-pressure surface, the calculated ultrasound flight time change value and the calculated ultrasound amplitude value. In the determined ultrasound flight time change value surface and the determined ultrasound amplitude value surface, coordination values of the concentration and the pressure with the corresponding ultrasound flight time change value and the corresponding ultrasound amplitude value can be obtained. At this time, using the ultrasound flight time change value and the ultrasound amplitude value, the concentration and the pressure can be calculated by a numerical analysis method using a Newton's method which is used as a solution for nonlinear equations. FIG. 7 shows an example of a curved surface of an ultrasound flight time change value contoured at a reference temperature, FIG. 8 shows an example of a curved surface of an ultrasound amplitude value contoured at a reference temperature, and FIG. 9 is a drawing exemplarily showing an ultrasound flight time change value and an ultrasound amplitude value by a temperature calibration equation of an ultrasound flight time change value and a temperature calibration equation of an ultrasound amplitude value according to an embodiment of the present invention. In FIG. 9, cases of 0.09, 0.11, 0.13, 0.14, 0.16, 0.18, 0.20, 0.22, 0.23 and 0.24 of an ultrasound amplitude value are shown in contour lines, and cases of −2.37, −1.79, −1.20, −0.62, −0.03, 0.56, 1.14, 1.73 and 2.31 of an ultrasound flight time change value are shown in contour lines. For example, as shown in a bold line and in a bold dotted line, when the ultrasound amplitude value is 0.14 and the ultrasound flight time change value is 0.56, the concentration and the pressure become the coordination values (i.e., approximately 0.875 and 1.00 bar) of a horizontal axis and a vertical axis at the crossing point of the two lines.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A method for determining concentration and pressure of respective gas consisting of multi-gas using emitting and receiving of ultrasound, comprising:

measuring a reference ultrasound flight time at a reference concentration, a reference temperature and a reference pressure for a target respective gas among respective gases consisting the multi-gas which is filled in a measuring space using an emitted ultrasound waveform and a received ultrasound waveform;

measuring ultrasound flight times at plural concentrations, temperatures and pressures in a state that concentration, temperature and pressure of the target respective gas are parameters;

obtaining an ultrasound flight time table comprising ultrasound flight time change values which are differences between the reference ultrasound flight time, which varies according to parameters of concentration, temperature and pressure, and the measured ultrasound flight time;

obtaining an ultrasound amplitude table comprising ultrasound amplitude values of a waveform of a predetermined sequence of the received ultrasound waveform at plural concentrations, temperatures and pressures in a state that concentration, temperature and pressure of the target respective gas are parameters; and calculating the concentration and the pressure of the target gas based on performing temperature compensations for the ultrasound flight time change values and the ultrasound amplitude values.

2. The method of claim 1, wherein the calculating of the concentration and the pressure of the target gas comprises:

obtaining a temperature compensation equation for an ultrasound flight time which makes the ultrasound flight time change values at the plural temperatures become the ultrasound flight time change value at the reference temperature;

obtaining a temperature compensation equation for an ultrasound amplitude which makes the ultrasound amplitude values at the plural temperatures become the ultrasound amplitude value at the reference temperature;

converting an ultrasound flight time change value measured at an arbitrary measuring temperature and an ultrasound amplitude value measured at an arbitrary measuring temperature into an ultrasound flight time change value at the reference temperature and an ultrasound amplitude value respectively by putting the same into the temperature compensation equation for the ultrasound flight time change value and the temperature compensation equation for the ultrasound amplitude respectively; and calculating the concentration and the pressure of the target gas by nonlinear equations using the ultrasound flight time change values at the reference temperature and the ultrasound amplitude values at the reference temperature.

\* \* \* \* \*